United States Patent
Wang et al.

(10) Patent No.: US 9,797,910 B2
(45) Date of Patent: Oct. 24, 2017

(54) ASSAY FOR DETERMINING ENDOGENOUS LEVELS OF ANALYTE IN VIVO

(71) Applicant: Merck Sharp & Dohme Corp., Rahway, NJ (US)

(72) Inventors: Weixun Wang, Metuchen, NJ (US); Bernard Karsten Choi, South Plainfield, NJ (US); Lucinda H. Cohen, Fanwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 75 days.

(21) Appl. No.: 14/888,982

(22) PCT Filed: Jun. 13, 2014

(86) PCT No.: PCT/US2014/042235
§ 371 (c)(1),
(2) Date: Nov. 4, 2015

(87) PCT Pub. No.: WO2014/204795
PCT Pub. Date: Dec. 24, 2014

(65) Prior Publication Data
US 2016/0084848 A1     Mar. 24, 2016

Related U.S. Application Data

(60) Provisional application No. 61/836,807, filed on Jun. 19, 2013.

(51) Int. Cl.
*G01N 33/53* (2006.01)
*G01N 33/68* (2006.01)

(52) U.S. Cl.
CPC ..... *G01N 33/6863* (2013.01); *G01N 33/6848* (2013.01); *G01N 2333/521* (2013.01); *G01N 2560/00* (2013.01)

(58) Field of Classification Search
None
See application file for complete search history.

(56) References Cited

U.S. PATENT DOCUMENTS

| 4,280,816 A | 7/1981 | Elahi |
| 2001/0019829 A1* | 9/2001 | Nelson ................. C12Q 1/6816 435/7.1 |
| 2006/0052310 A1 | 3/2006 | Wallner |
| 2008/0253996 A1 | 10/2008 | Boschert et al. |
| 2009/0316992 A1 | 12/2009 | Wheelock |
| 2012/0100554 A1 | 4/2012 | Lillard et al. |

OTHER PUBLICATIONS

Valenzuela-Fernandez et al. J. Biol Chem. 2002 vol. 277, p. 15677-15689.*
Zhao, S. et al., A Comprehensive Analysis of CXCL12 Isoforms in Breast Cancer 1,2,3, Translational Oncology, 2014, p. 429-438, vol. 7, No. 3.

* cited by examiner

*Primary Examiner* — Jacob Cheu
(74) *Attorney, Agent, or Firm* — Janet E. Fair; Catherine D. Fitch

(57) ABSTRACT

The present invention relates to an assay for determining endogenous levels of analyte in vivo. In particular, the present invention is directed to an assay for determining endogenous levels of stromal cell-derived factor (SDF-1) isoforms in vivo.

16 Claims, 10 Drawing Sheets

SEQUENCE LISTING

```
<160> NUMBER OF SEQ ID NOS: 8

<210> SEQ ID NO 1
<211> LENGTH: 68
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 72
<212> TYPE: PRT
<213> ORGANISM: Homo sapiens

<400> SEQUENCE: 2

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45
```

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 3
<211> LENGTH: 68
<212> TYPE: PRT
<213> ORGANISM: Mus musculus

<400> SEQUENCE: 3

Lys Pro Val Ser Leu Ser Tyr Arg Cys Pro Cys Arg Phe Phe Glu Ser
1               5                   10                  15

His Ile Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 4
<211> LENGTH: 72
<212> TYPE: PRT
<213> ORGANISM: Mus musculus

<400> SEQUENCE: 4

Lys Pro Val Ser Leu Ser Tyr Arg Cys Pro Cys Arg Phe Phe Glu Ser
1               5                   10                  15

His Ile Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Leu Lys Met
65                  70

<210> SEQ ID NO 5
<211> LENGTH: 68
<212> TYPE: PRT
<213> ORGANISM: Rattus norvegicus

<400> SEQUENCE: 5

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Ser Asn Asn Arg Gln
        35                  40                  45

Val Cys Ile Asp Pro Lys Leu Lys Trp Ile Gln Glu Tyr Leu Asp Lys
    50                  55                  60

Ala Leu Asn Lys
65

<210> SEQ ID NO 6
<211> LENGTH: 72

```
<212> TYPE: PRT
<213> ORGANISM: Rattus norvegicus

<400> SEQUENCE: 6

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Ser Asn Asn Arg Gln
            35                  40                  45

Val Cys Ile Asp Pro Lys Leu Lys Trp Ile Gln Glu Tyr Leu Asp Lys
        50                  55                  60

Ala Leu Asn Lys Arg Leu Lys Met
65                  70

<210> SEQ ID NO 7
<211> LENGTH: 68
<212> TYPE: PRT
<213> ORGANISM: Macaca mulatta

<400> SEQUENCE: 7

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65

<210> SEQ ID NO 8
<211> LENGTH: 72
<212> TYPE: PRT
<213> ORGANISM: Macaca mulatta

<400> SEQUENCE: 8

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys Arg Phe Lys Met
65                  70
```

ASSAY FOR DETERMINING ENDOGENOUS LEVELS OF ANALYTE IN VIVO

FIELD OF THE INVENTION

The present invention relates to an assay for determining endogenous levels of an analyte in vivo. In particular, the present invention is directed to an assay for determining endogenous levels of stromal cell-derived factor (SDF-1) isoforms in vivo.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "23509-US-PSP.txt", a creation date of May 2, 2013 and a size of 5,599 bytes. The Sequence Listing filed via EFS-Web is part of the specification and incorporated in its entirety by reference herein.

BACKGROUND

Stromal cell-derived factor (SDF-1) exists in many isoforms that are differentially distributed in various tissues. The highest expressed isoforms appear to be α and β which differ only at the carboxy terminus, with the β isoform being longer by four amino acid residues (72 vs. 68 residues). Both isoforms are found in circulation, but are differentially processed at the carboxy terminus by an unknown peptidase in serum. In vitro studies have shown that the terminal lysine of recombinant α isoform (K68) is immediately removed upon incubation in serum, whereas the recombinant β isoform is resistant to similar degradation. The amino termini of both isoforms, however, are vulnerable to cleavage by dipeptidyl peptidase IV (DPP-IV) with cleavage efficiencies ($k_{cat}/K_m$) higher than that of GLP-1. Similar to GLP-1, the removal of the two amino terminal residues inactivates SDF-1 by disruption of its receptor binding with CXCR4 and subsequent activation.

Recently, there has been increasing interest in the investigation of suppression of SDF-1 inactivation with DPP-IV inhibition. To date, however, most efforts have been limited to in vitro studies or in vivo studies with infused SDF-1 at superphysiological concentrations. These studies, though insightful, failed to provide direct evidence on suppression of endogenous SDF-1 inactivation by in vivo DPP-IV inhibition with therapeutic agents. The hindrance to such efforts is not the lack of specific assays that differentiate SDF-1 isoforms from their DPP-IV cleaved forms; many previous in vitro kinetics studies successfully employed mass spectrometry (MS) based methods to generate sequence specific measurements. The sensitivity of these MS methods, however, was not suitable for measurement of SDF-1 at endogenous levels (often sub nanomolar) in complex biological matrices such as plasma and serum. Instead, the endogenous SDF-1 isoforms in circulation were often quantified with antibody based immunoassays, which lacked the specificity to differentiate intact SDF-1 isoforms from DPP-IV cleaved ones and thus were inadequate for in vivo DPP-IV inhibition studies.

SUMMARY

The inventors have developed a tandem mass spectrometry based assay with sufficient sensitivity to quantify isoforms of SDF-1 at the endogenous level while retaining sequence specificity that is required to distinguish intact SDF-1 isoforms from its NH$_2$-terminal truncated inactive form.

The assay described herein, in certain embodiments, can include the following steps: preparing a mixture of an internal standard of an SDF-1 isoform, a plasma sample containing endogenous SDF-1 and an immobilized antibody; incubating the mixture; separating out the immobilized antibody bound with SDF-1 isoform; releasing the SDF-1 isoform from the immobilized antibody; introducing the SDF-1 isoform to a mass spectrometer; and determining the endogenous levels of the SDF-1 isoform in vivo.

In one embodiment of the method described herein, an intact and NH$_2$ terminus cleaved SDF-1 isoform is enriched from plasma through binding to immobilized antibodies prior to analysis on a triple quadrupole (QQQ) mass spectrometer. The assay exhibits a broad linear range (103) with a lower limit of quantification (LLOQ) at low picomolar (pM) level, which is sufficiently lower than the endogenous concentration.

DESCRIPTION

Figure 1:
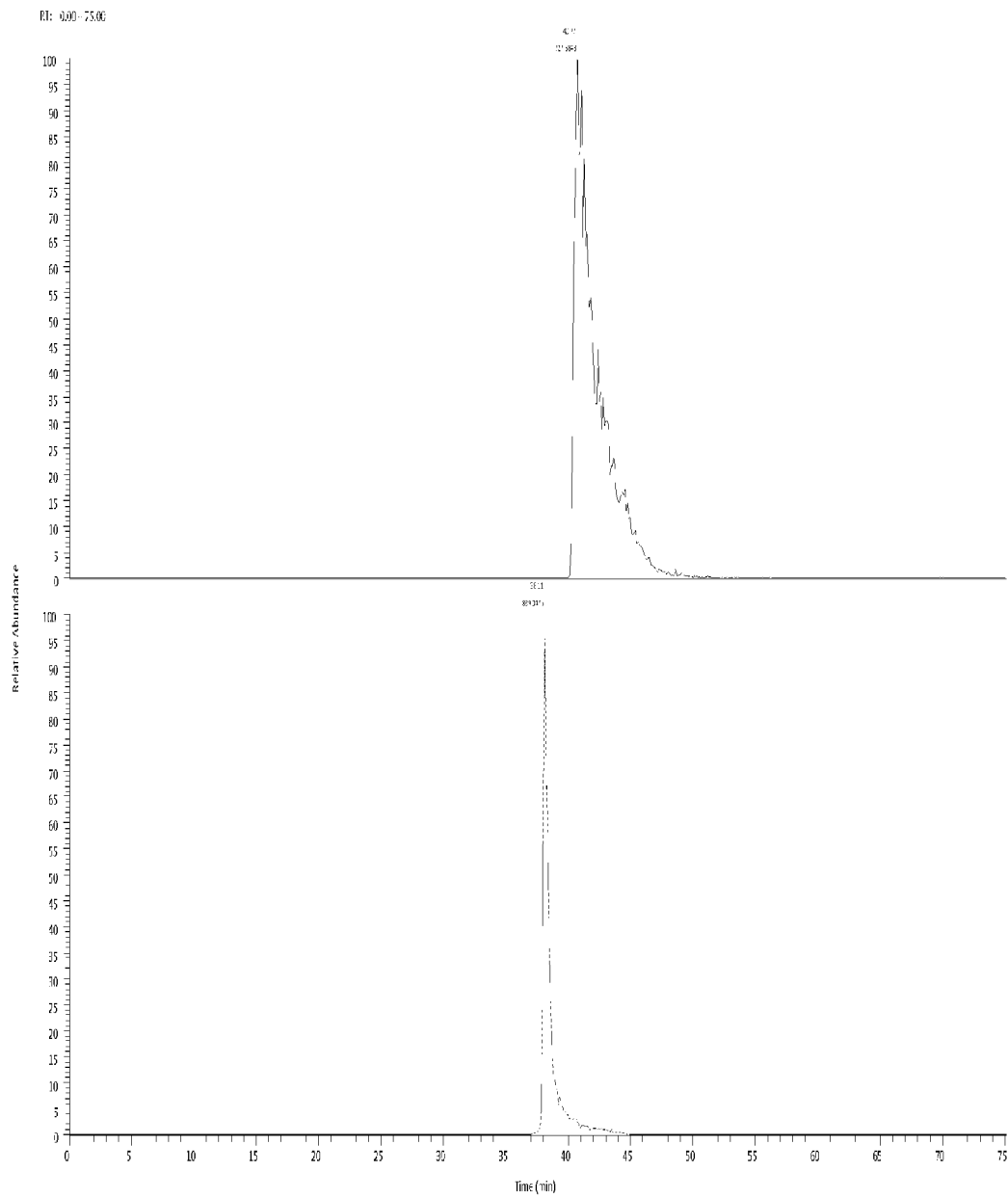
FIG. 1 represents characterization of synthetic SDF-1α standard with and without long range disulfide bond formation. The top panel is extracted ion chromatogram (XIC) of SDF-1α 1-67 without disulfide bond formation; the bottom panel: XIC of SDF-1α 1-67 after long range disulfide bonds are formed by oxidation with a redox buffer.

The present invention may be understood even more readily by reference to the following detailed description of exemplary embodiments of the invention and the examples included therein.

In general, there are two strategies involved in protein quantification with mass spectrometry: "bottom-up" and "top-down". In the bottom-up approach, proteins are first enzymatically digested and then quantified through signals of representative peptides. In the top-down approach, intact proteins are directly quantified without being enzymatically digested first. Practically speaking, top-down approach is a more straightforward operation with fewer steps involved than the bottom-up approach, but the sensitivity of the top-down approach diminishes when molecular mass of analytes increases. For proteins with higher masses, the bottom-up approach is the ideal method because of more favorable chromatographic behavior and ionization efficiency of ESI MS for peptides than for proteins. However, because it only relies on a handful of selected peptides for quantification, the bottom-up approach it rarely distinguishes protein isoforms or truncated forms of the same protein.

For the assay described herein the inventors used the "top-down" approach without converting the SDF-1 isoform to peptide fragments through enzymatic digestion and still achieved the desired sensitivity. To achieve optimal sensitivity and absolute quantification, the assay couples immunoaffinity enrichment of SDF-1 isoforms with stable isotope dilution LC-MS quantification. Leveraging specificity by tandem mass spectrometry and simplification of the background by affinity purification of peptide analytes, the hybrid assay format has been shown to be highly effective in quantifying low abundance proteins/peptides that are not amenable to immunoassays.

Stromal Cell-derived factor 1 (SDF-1) is a CXC chemokine that binds to the CXCR4 receptor. Recent publication indicates that the SDF-1/CXCR4 signaling pathway plays a pivotal role during development and in many pathophysiological conditions including hematopoiesis, blood vessel formation, cancer metastasis, angiogenesis and HIV infection. The highest expressed forms are SDF-1α and SDF-1β. Additionally, four additional human SDF-1 isoforms derived from alternative splicing events, SDF-1γ, SDF-1δ, SDF-1ε and SDF-1φ. These SDF-1 splice variants all share the same first three exons but contain different fourth exons. The human SDF-1 gene spans over 88 kilobase-pairs on chromosome 10. SDF-1 isoforms. SDF-1α and SDF-1β share similar expression patterns and the highest expression were detected in liver, pancreas and spleen. SDF-1γ seems to be the human orthologue of recently isolated rat SDF-1γ, and its expression was only detected in the heart. SDF-1δ expression can be detected in several adult tissues but the highest expression was detected in fetal liver.

The methods described herein describe an assay for determining endogenous levels of SDF-1 isoforms in vivo. Such isoforms are discussed above and include, but are not limited to, SDF-1α, SDF-1β, SDF-1γ, SDF-1δ, SDF-1ε and SDF-1φ.

The assay described herein, in certain embodiments, can include the following steps: preparing a mixture of an internal standard of an SDF-1 isoform, a plasma sample containing endogenous SDF-1 and an immobilized antibody; incubating mixture; separating out immobilized antibody bound with SDF-1 isoform; releasing the SDF-1 isoform from the antibody; introducing the SDF-1 isoform to a mass spectrometer; and determining the endogenous levels of the SDF-1 isoform in vivo.

As used herein the phrase internal standard refers to a chemical substance that is added in a constant amount to samples. For preparing the mixture of an internal standard of an SDF-1 isoform, a plasma sample containing endogenous SDF-1 and an immobilized antibody, suitable internal standard peptides include, but are not limited to, isotope-labeled peptides representing the sequences of SDF-1 isoforms. For example in one embodiment the internal standard peptides include stable isotope-labeled internal standard peptides representing the sequences of SDF-1α 1-67 and 3-67.

Plasma samples can be obtained from any species which determination of endogenous SDF-1 isoforms is desired. Such species include human and non-human animals, including but not limited to, mice, rats, dogs, cats, cows, horses and non-human primates such as monkeys and apes. Human and Rhesus SDF-1α are represented in SEQ ID NO. 1 and SEQ ID NO. 3. Human and Rhesus SDF-1β are represented in SEQ ID NO. 2 and SEQ ID NO. 4. Mouse SDF-1α is represented in SEQ ID NO. 5. Mouse SDF-1β is represented in SEQ ID NO. 6. Rat SDF-1α is represented in SEQ ID NO. 7. Rat SDF-1β is represented in SEQ ID NO. 8. Prior to being put into the mixture the plasma can be diluted with a buffer.

As used herein, the term immobilized refers to, being physically or chemically attached to a solid support. For example an immobilized antibody refers to an antibody that is physically or chemically attached to a solid support. Suitable immobilized antibodies include any suitable SDF-1 antibodies secured to a solid support. Support materials can comprise a wide range of material, either biological, non-biological, magnetic, organic, inorganic, or a combination of any of these. For example, the support material may be a polymerized Langmuir Blodgett film, functionalized glass, Si, Ge, GaAs, GaP, $SiO_2$, $SiN_4$, modified silicon, or any one of a wide variety of gels or polymers. Support materials can be planar crystalline support materials such as silica based support materials (e.g. glass, quartz, or the like), or crystalline support materials used in, e.g., the semiconductor and microprocessor industries, such as silicon, gallium arsenide and the like. Silica aerogels can also be used as support materials, and can be prepared by methods known in the art. Aerogel support materials may be used as free standing substrates or as a surface coating for another support material.

A support material can take any form or shape and typically is a plate, slide, bead, pellet, disk, particle, strand, precipitate, membrane, optionally porous gel, sheets, tube, sphere, container, capillary, pad, slice, film, chip, multiwell plate or dish, optical fiber, etc. Although typically the support material takes an inanimate form, for some attachment peptide applications such as flow cytometry or in situ hybridization, it can be any form that is rigid or semi-rigid. The support material may contain raised or depressed regions on which a capture probe is located. The surface of the support material can be etched using well known techniques to provide for desired surface features, for example trenches, v-grooves, mesa structures, or the like.

A solid support may be of any suitable composition to which the attachment molecule may be applied. It may be pretreated or functionalized prior to application of the attachment/molecule peptide to facilitate binding of the attachment molecules, or for any other desired purpose, such as fostering conditions favorable for the activity or any other desired property of the entity or avoiding undesired interactions with other entities. Many such surface treatments and/or functionalizations are known in the art and selection of a suitable treatment and/or functionalization will depend upon the identity and characteristics of the attachment molecule/peptide and entity and upon the attendant conditions and desired activity.

With regard to the immobilized antibodies described herein the solid support is a bead, preferably a magnetic bead that can bind to SDF-1 antibodies. In certain embodiments polyclonal SDF-1 antibodies are covalently bound to superparamagnetic beads. Such superparamagnetic beads include DYNABEADS (Invitrogen). In one embodiment, polyclonal anti-SDF-1α antibody (RnD Systems) are covalently bound to tosyl-activated Dynal M-280 beads (Invitrogen) according to the manufacturer's instructions.

Once the plasma, immobilized SDF-1 antibody and internal standard are mixed together, the mixture is incubated until the SDF-1 isoform in the plasma is bound to the immobilized antibody of the particular SDF-1 isoform. Incubation times can range from a couple of hours to a few days. In certain embodiments, incubation can take 10, 12, 14, 16, 18, 20, 22 or 24 hours. In one embodiment described herein the mixture was incubated for 16 hours. As used herein, the term bound refers to being chemically attached.

Once the mixture has been incubated and the SDF-1 isoform has been bound to the immobilized antibody on the solid support, the solid support is separated from the mixture and washed. In certain embodiments wherein magnetic beads are used as the solid support, a magnet can be used to separate the beads out of the mixture. A magnet can be employed for this purpose.

After separating out the immobilized antibody bound with SDF-1 isoform from the mixture, the SDF-1 isoform is released from the SDF-1 antibody. In certain embodiments, the release of the SDF-1 isoform from the SDF-1 antibody can be done with an acid wash. However, the conditions under where the SDF-1 isoform is released from the SDF-1 antibody will depend on the SDF-1 isoform and the SDF-1 antibody used. In certain embodiments were an acid wash is used, suitable acids include but are not limited to, acetic acid, hydrochloric acid, trufluoroacetic acid, methanesulfonic acid, ethanesulfonic acid, benzenesulfonic acid, p-toluenesulfonic acid, trifluoromethanesulfonic acid, polystyrene sulfonic acid, citric acid, formic acid, gluconic acid, lactic acid, oxalic acid.

Once the SDF-1 isoform has been eluted, the SDF-1 isoform is introduced in a mass spectrometer in order to quantify the endogenous levels of SDF-1 isoform in vivo. The term "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z").

The ions may be detected using several detection modes. For example, selected ions may be detected using a selective ion monitoring mode (SIM), or alternatively, ions may be detected using a scanning mode, e.g., multiple reaction monitoring (MRM) or selected reaction monitoring (SRM).

Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments the eluted isoforms are analyzing using liquid chromatography/mass spectroscopy (LCMS). In certain embodiments, the measurements of intact and DPP-IV cleaved SDF-1 isoforms were multiplexed in a single method on a QQQ mass spectrometer. Through isotope dilution with stable isotope labeled internal standards, the assay generates absolute quantification of the SDF-1 isoforms The assay described herein generates absolute quantification of the analytes. The assay described herein has a linear range for quantification relevant to the physiological level of SDF-1 analytes. The assay described herein has a linear range spanning three orders of magnitude, spanning picamolar per liter to nanomolar per liter. In certain embodiments the linear range of the assay described herein spans 20 pmol/L to 20 nmol/L. Because the assay described herein was able to achieve a lower limit of quantification in the pico molar range, the assay was capable to have the quantitate specificity necessary to measure endogenous levels of SDF-1 in vivo.

The assay described herein is capable of detecting SDF-1 at concentrations of less than 5 nmol/L in the sample. In certain embodiments, the assay described herein is capable of detecting SDF-1 at concentrations of less than 4 nmol/L in the sample. In other embodiments, the assay described herein is capable of detecting SDF-1 at concentrations of less than 3 nmol/L in the sample. In yet other embodiments, the assay described herein is capable of detecting SDF-1 at concentrations of less than 2 nmol/L in the sample. In still other embodiments, the assay described herein is capable of detecting SDF-1 at concentrations of less than 1 nmol/L in the sample.

Also described herein is a method for determining suppression of inactive SDF-1 isoforms by DPP-IV inhibition in vivo comprising the steps of: drawing a first plasma sample from a subject; administering to a subject a DPP-IV inhibitor; drawing a second plasma sample from a subject; assaying the first and second samples with the following assay:

a. preparing a mixture of an internal standard of an SDF-1 isoform, a plasma sample containing endogenous SDF-1 and an immobilized antibody; incubating mixture;
b. separating out immobilized antibody bound with SDF-1 isoform; releasing the SDF-1 isoform from the antibody;
c. introducing the SDF-1 isoform to a mass spectrometer; and
d. determining the endogenous levels of the SDF-1 isoform in vivo.; and comparing the amount of intact SDF-1 isoform from the DPP-IV cleaved inactive form.

Although, plasma samples are discussed above, suitable test samples may include any test sample that may contain the analyte of interest. In some preferred embodiments, a sample is a biological sample; that is, a sample obtained from any biological source, such as an animal, a cell culture, an organ culture, and the like. In certain preferred embodiments, samples are obtained from a mammalian animal, such as a dog, cat, horse, etc. Particularly preferred mammalian animals are primates, most preferably humans. Particularly preferred samples include blood, plasma, serum, urine, saliva, tears, cerebrospinal fluid, or other body fluid or tissue samples. Such samples may be obtained, for example, from a patient; that is, a living person presenting oneself in a clinical setting for diagnosis, prognosis, or treatment of a disease or condition. The test sample is preferably obtained from a patient, for example, serum or plasma.

DPP-IV inhibitors that can be administered to a subject include, but are not limited to, sitagliptin, vildagliptin, saxagliptin, alogliptin, denagliptin, carmegliptin, dutogliptin, melogliptin, linagliptin, and pharmaceutically acceptable salts thereof

EXAMPLES

Stable Isotope Labeled Peptide Standards

Stable isotope-labeled internal standard peptides representing the sequences of SDF-1α 1-67 and 3-67 were synthesized and analyzed for purity and amino acid content (CPC Scientific). Subsequent calculations of concentration were based on the purity assessment and weight measurement.

Because the lysine residue at the carboxy terminus of SDF-1α is removed instantly by an unknown carboxypeptidase in plasma, SDF-1α sequences without the terminal lysine, namely 1-67 and 3-67, were selected for quantification. Stable isotope-labeled peptides were synthesized for both SDF-1α 1-67 and 3-67 with five heavy isotope labeled leucine (13C615N1) residues distributed along the sequences (at positions 36, 42, 55, 62, and 66). The stable isotope-labeled standards, though chemically identical, are heavier by 35 Da than endogenous SDF-1α forms. The cysteine residues were synthesized in sulfhydryl forms (non-reduced and without being alkylated) so that two pairs of long range disulfide bonds, Cys9-Cys34 and Cys11-Cys50, could be formed under mildly oxidative environment. Shown below are SDF-1α forms wherein the Cys9-Cys34 and Cys11-Cys50 are underlined.

KPVSLSYRCPCRFFESHVARANVKHLKILNTPNCALQIVARLKNNNRQVC

IDPKLKWIQEYLEKALNVSLSYRCPCRFFESHVARANVKHLKILNTPNCA

LQIVARLKNNNRQVCIDPKLKWIQEYLEKALN

Formation of Intra-Molecular Disulfide Bonds with a Glutathione Redox Buffer System Reduced and oxidized glutathione were dissolved in 0.1 M Tris.HCl buffer at pH 8.5 at final concentration 10.0 mM and 1.0 mM respectively. Heavy isotope labeled SDF-1α standards were reconstituted in the glutathione redox buffer at 125 µg/mL and stored at room temperature for 24 hours for disulfide bond formation and refolding.

High Resolution LC/MS Characterization of Unfolded and Refolded SDF-1α Isoforms

Unfolded and refolded heavy labeled standards of SDF-1α were analyzed by a reverse phase nano-HPLC coupled to a LTQ-FTICR hybrid mass spectrometer (LTQ-FT Ultra, ThermoFisher). Approximately 1 pmol of SDF-1α standards were injected with an auto-sampler (Series 1100, Agilent, CA) onto a nano-LC column packed with BioBasic® C8 media (5 cm×75 µm, New Objective, MA). A micro-flow HPLC pump (Agilent Series 1100) delivered a binary gradient increasing from 0% hydrophobic phase (0.1 M acetic acid in acetonitrile) to 50% hydrophobic phase at a rate of 1%/min while maintaining the flow rate at 1 µl/min. Peptides eluting from the nano-LC column were introduced into the mass spectrometer by electrospray ionization using a 3-kV needle voltage, heated metal capillary temperature of 270° C., and tube lens voltage at 120 V. Ion injection times into linear ion trap were adjusted by the instrument automatic gain control (1×107 arbitrary unit setting) with a maximum accumulation time not to exceed 1 second. Ions were passed to the FTICR cell, and full scan spectra with mass-to-charge ratio (m/z) from 300 to 2,000 were acquired approximately every 3 second. While the full scan MS spectra were acquired in the FTICR cell at an instrument-resolving power of 50,000, data-dependent MS/MS scans of the four most intense precursor ions in the preceding full MS scan were collected in the linear ion trap.

Figure 2:
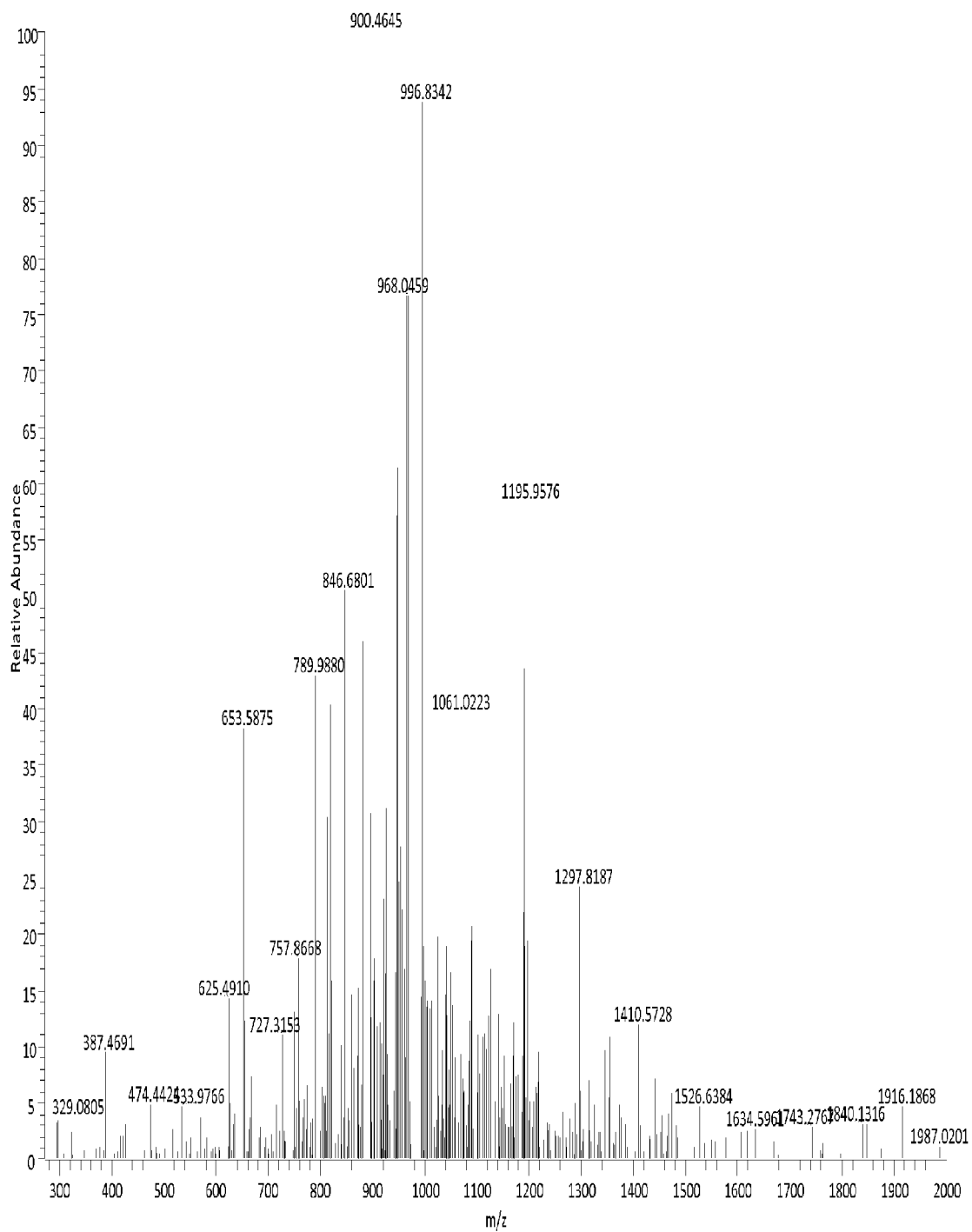
FIG. 2 represents a collision induced disassociation (CID) spectrum of SDF-1α 1-67 without disulfide bonds.
Figure 3:
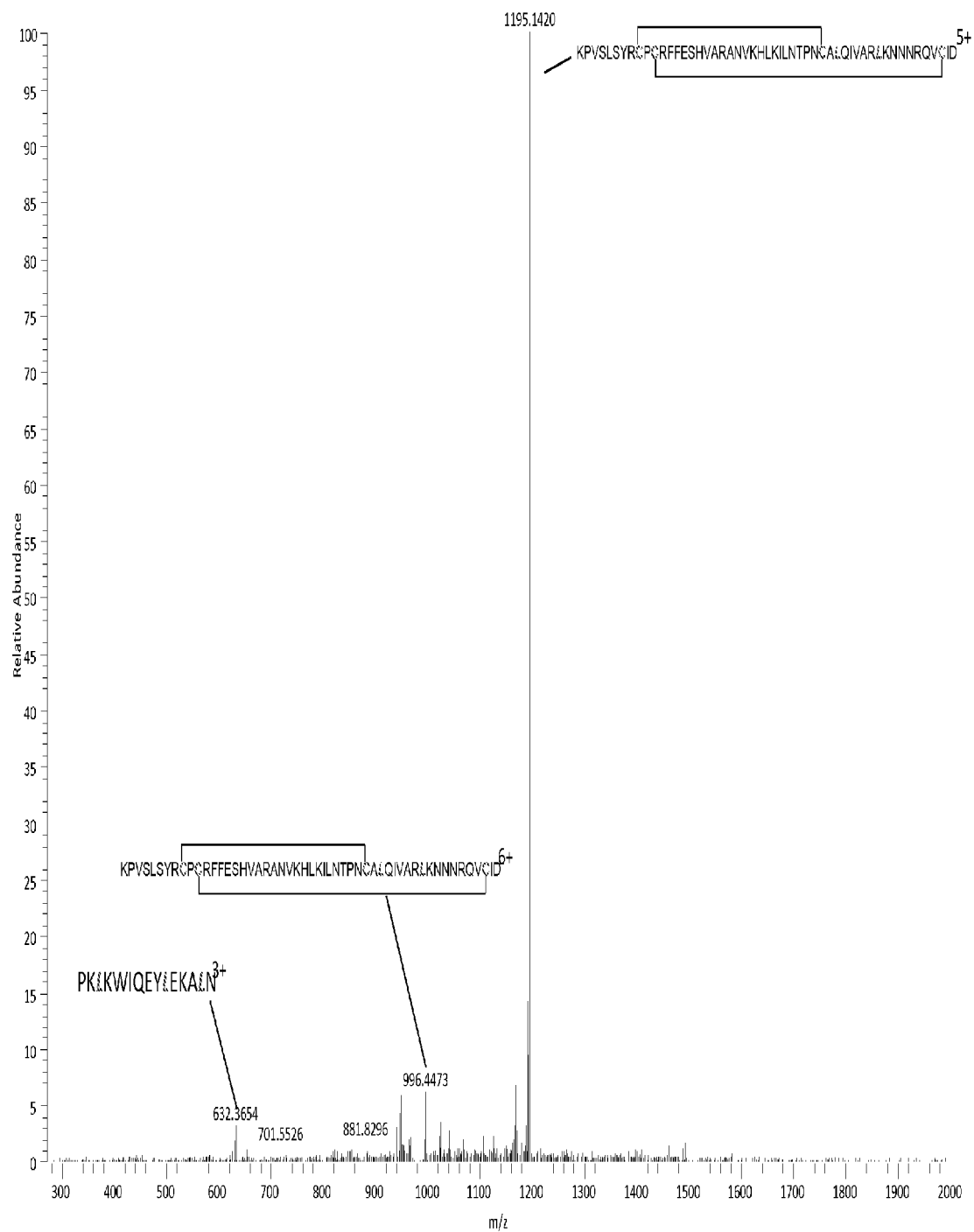
FIG. 3 represents a CID spectrum of SDF-1α with long range disulfide bonds in correct configuration.

A glutathione based redox system was optimized to slowly oxidize the cysteine residues to minimize short range and intermolecular disulfide bond formation so that the peptide standards were refolded to native and globular structures. The refolded peptide standards were characterized with a hybrid LTQ-FTMS platform with a nano-flow LC system providing front end separation. In alternating MS scans, high resolution full MS spectra were acquired with the FTICR analyzer and CID MS/MS spectra were collected with the linear ion trap. Accurate mass measurement was used to confirm the formation of the disulfide bonds, e.g. for refolded stable isotope labeled SDF-1α 1-67 standard, the difference between measured mass (7861.260) and calculated mass (7861.254) is ~1 ppm. Corresponding CID fragment ion spectra verified the correct configuration of the disulfide bonds. In the MS/MS spectrum of refolded SDF-1α 1-67, all three fragment ions in the CID MS/MS spectrum were assigned with delta mass less than 0.5 Da. All three fragment ions (b525+, b526+, and y152+) were derived from the dissociation of the amide bond between Asp52 and Pro51 (FIGS. 1-3). The scarcity of fragment ions and backbone amide bond breakages is obvious when the MS spectrum of refolded SDF-1α 1-67 standard is compared with the MS/MS spectrum of SDF-1α 1-67 standard prior to being refolded. Both the covalent links between cysteine residues and amide backbone need to be dissociated to produce fragment ions, which is not common in CID fragmentation. The dominance of fragment ions resulted from the breakage of amide bond between Asp52 and Pro51 was also expected because the dissociation of the amide bond $NH_2$ terminal to proline residue is often favored in CID. The refolded SDF-1α 3-67 had a similar fragmentation pattern with dominant fragment ions being b505+ and y152+, resulting from the dissociation of the amide bond between Asp50 and Pro51. In peptide sequencing, the lack of fragment ions in CID MS/MS spectra due to disulfide bond formation poses as a challenge; in peptide quantification with MRM, however, it provides a unique opportunity in reducing signal loss because the signal of parent ion is spread to very limited number of product ions.

Besides fragmentation pattern, the chromatographic behaviors of SDF-1α with and without disulfide bonds were also significantly different. The extracted ion chromatogram (XIC) of the SDF-1α sequences without refolding showed a broad peak with significant rear end tailing, whereas the XIC of the refolded SDF-1α sequences exhibited a sharp, symmetrical peak (FIGS. 1-3). FIG. 1 shows characterization of synthetic SDF-1α standard with and without long range disulfide bond formation. The top panel is extracted ion chromatogram (XIC) of SDF-1α 1-67 without disulfide bond formation; the bottom panel: XIC of SDF-1α 1-67 after long range disulfide bonds are formed by oxidation with a redox buffer. FIG. 2 represents a collision induced disassociation (CID) spectrum of SDF-1α 1-67 without disulfide bonds. The precursor ion is 984.1681 [M+8H]8+. FIG. 3 represents a CID spectrum of SDF-1α with long range disulfide bonds in correct configuration. The precursor ion is 983.6645 [M+8H]8+. Because of the restraint by disulfide bonds, CID only yielded very limited fragment ions, b525+, b526+, and y152+, with all being products from the fragmentation of the amide bond between Asp52 and Pro53.

The difference in LC elution profile could be attributed to the difference in peptide conformation: the structure of the peptide was probably random coil (a collection of many random structures without a specific shape) before being properly folded with the help of disulfide bond formation, after being refolded with proper disulfide bond configuration the peptide adopted a globular structure (a unique shape). The singularity in tertiary structure leads to the singularity in hydrophobicity and thus the narrow, symmetrical LC elution profile that resembles those of short peptides and small molecules.

Affinity Purification of SDF-1α Isoforms

Polyclonal anti-SDF-1α antibody (RnD Systems) was covalently bound to tosyl-activated Dynal M-280 beads (Invitrogen) according to the manufacturer's instructions. In each analysis, 100 μL of plasma was first diluted with 400 μL of Dulbecco's PBS buffer with 0.1% Tween® 20 (v/v), 200 fmol of heavy isotope labeled SDF-1α standards were then spiked in and mixed thoroughly with the diluted plasma though vortex. Twenty five microliter of antibody-conjugated beads was added to each sample for immunoaffinity enrichment. Following incubation for 16 hours at 4° C. with rotation, the beads were washed twice with 500 μL 50 mmol/L $(NH_4)_2CO_3$, pH 8.3 and twice with 500 μL water. The bound SDF-1α isoforms were eluted with 50 μL 2% acetic acid (2 hours, room temperature, with rotation).

Liquid Chromatography Tandem Mass Spectrometry

Eluted peptides were analyzed in SRM mode using a Thermo Vantage triple quadrupole instrument with the four m/z transitions with dwell time of 50 ms each. The transitions tracking human and murine SDF-1α isoforms and their corresponding isotope-labeled standards are listed in the table below and shown in FIG. 4.

TABLE 1

| SRM Transition | Parent | Q1 m/z | Product | Q3 m/z |
|---|---|---|---|---|
| #1 | Endogenous SDF-1α 3-67 | 951.6 (8+) | → Light $b_{50}$ | 1147.9 (5+) |
| #2 | Heavy SDF-1α 3-67 | 956 (8+) | → Heavy $b_{50}$ | 1150.7 (5+) |
| #3 | Endogenous SDF-1α 1-67 | 979.83 (8+) | → Light $b_{52}$ | 1193.2 (5+) |
| #4 | Heavy SDF-1α 1-67 | 984.2 (8+) | → Heavy $b_{52}$ | 1196 (5+) |

Peptides were loaded directly onto an analytical nanospray column (BioBasic® C8, 50 mm by 75 μm ID, New Objective, MA) with 0.1% formic acid in water at 2 μL/min. After five minutes of loading, the peptides were eluted off the column with a linear gradient to 50% acetonitrile, 0.1% formic acid over 5 min at 1 μL/min. Ion chromatograms (XICs) of both SRM transitions and calculated peak area ratios between endogenous SDF-1α isoforms and their heavy standards using LC-Quan™ (ThermoFisher) version 2.0.7 were integrated extracted. The equation (peak area ratio)(2 nmol/L) was used to calculate the concentrations of endogenous SDF-1α isoforms in the original sample, in nmol/L.

Figure 4:
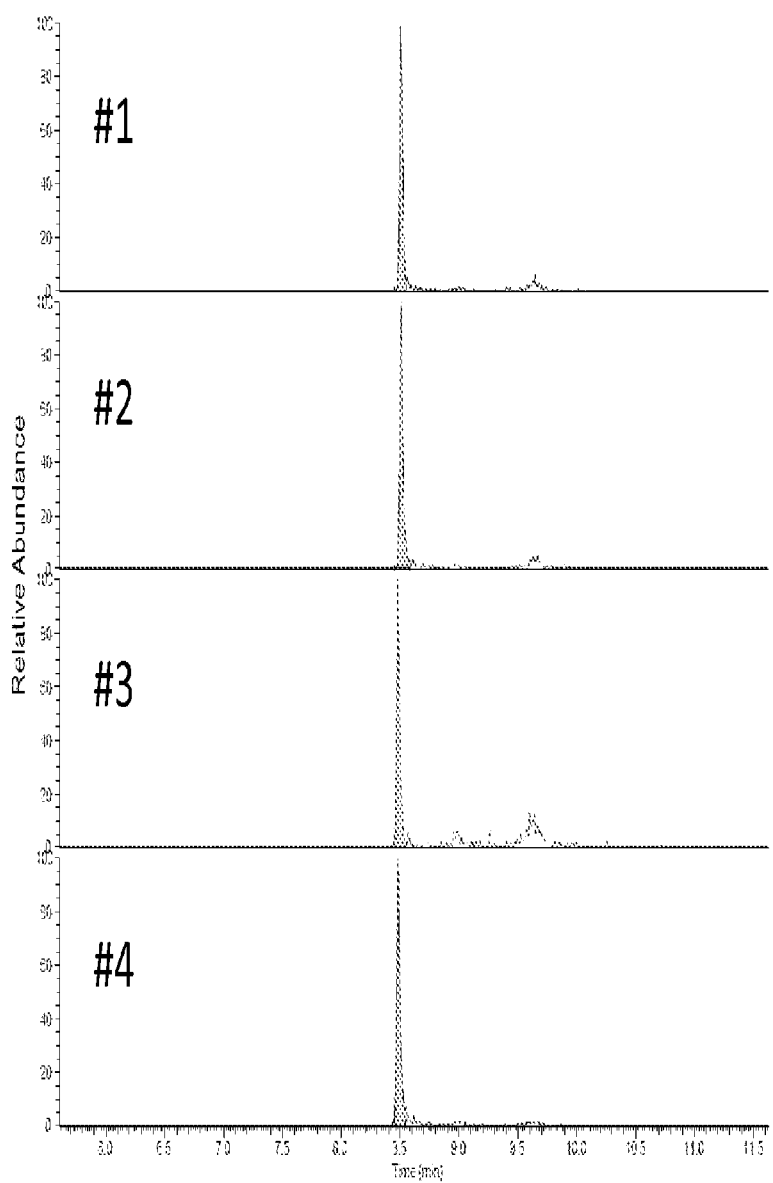
FIG. 4 represents selected ion monitoring (SRM) coupled with isotope dilution for the quantification of intact and DPP-IV processed SDF-1α.

LC-MS Isotope Dilution Quantification of SDF-1α Isoforms in Human, Rhesus, and Murine Plasma A SRM method was established on a QQQ instrument with four alternating Q1→Q3 transitions tracking fragmentations of SDF-1α 1-67 and 3-67 and their stable isotope labeled standards (Table 1). To effectively enrich SDF-1α isoforms from plasma and achieve optimal sensitivity for quantification of endogenous SDF-1α forms, an immunoaffinity enrichment step was employed with an anti-SDF-1α antibody prior to LC-MS/MS analysis. Specifically, the plasma was first spiked with fixed amount of stable isotope labeled SDF-1α standards (for both intact and $NH_2$-terminal truncated forms, at plasma conc. of 2 nmol/L), an anti-SDF-1α antibody conjugated to paramagnetic beads was then used to selectively bind and enrich SDF-1α from the background and the elutent was analyzed by LC-MS/MS analysis. An example of the total ion current chromatogram of SRM transitions measuring the endogenous SDF-1α forms and their respective isotope labeled standards is illustrated in FIG. 4. The linearity and limit of quantification (LOQ) of the LC-MS/MS assay were evaluated with a "reverse standard curve" where refolded heavy SDF-1α standards were spiked in human plasma at concentrations ranging from 1 pmol/L to 50 nmol/L.

Figure 5:
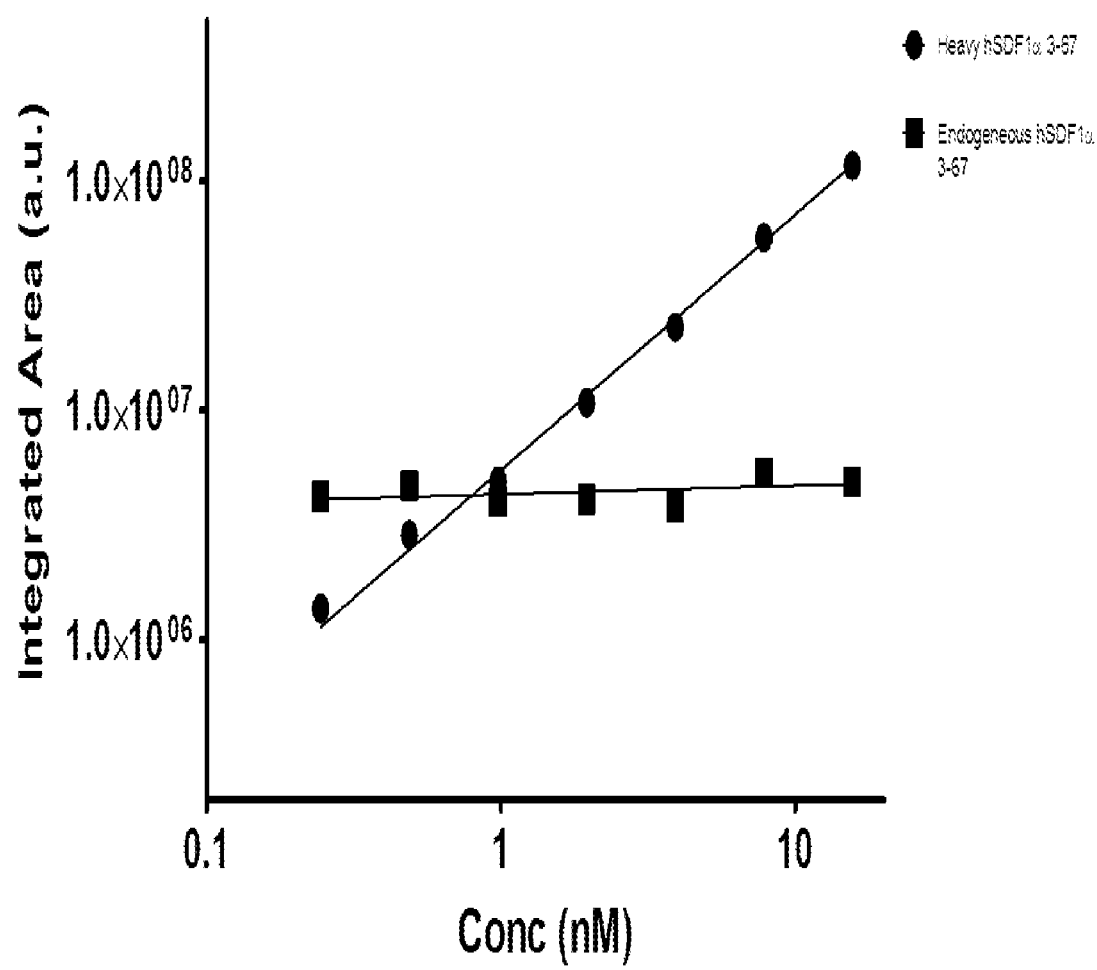
FIG. 5 represents concentration-response relationship in human plasma of LC-MS/MS response of stable isotope labeled internal standard of SDF-1α 3-67 vs. spiked concentration. Heavy isotope labeled internal standard was spiked in plasma at different concentrations prior to immunoaffinity enrichment and LC-MS/MS analysis.

An example of the LC-MS response, integrated peak area (AUC), against spiked concentrations for SDF-1α 3-67 heavy isotope-labeled standard is plotted in FIG. 5. The linear range of the assay spanned 3 orders of magnitude, from 20 pmol/L to 20 nmol/L. The level of endogenous SDF-1α 3-67 in plasma, represented by the horizontal line in the figure, was determined as 0.96 nmol/L (% CV=5.0%, N=12), which is within the quantitative range of the analysis. The lower LOQ of the assay, 20 pmol/L (% CV=12.2%, N=3), was determined according to the method described by Currie, L. A. *Anal Chem* 1968, 40, 586-593. Because of the complete overlap between human and rhesus SDF-1α sequences, the assay can be used for quantification of SDF-1α forms in rhesus plasma without modification. A reverse standard curve using rhesus plasma as background matrix yielded the same quantitative range and LOQ as the standard curve with human plasma as background, with the endogenous SDF-1α 3-67 level in pooled rhesus plasma determined at 0.65 nmol/L (% CV=4.9%, N=12).

Figure 6:
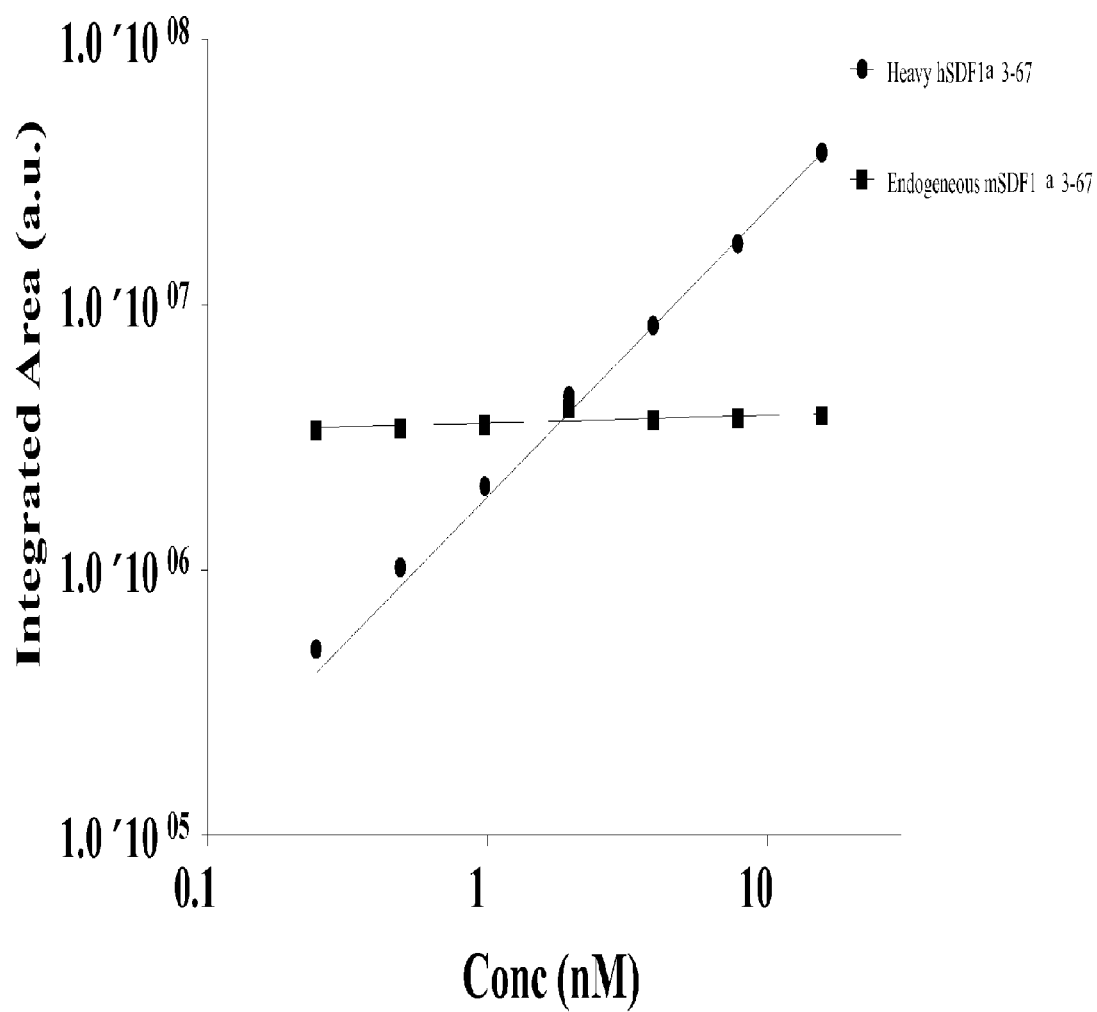
FIG. 6 represents concentration-response relationship in mouse plasma of LC-MS/MS response of stable isotope labeled internal standard of SDF-1α 3-67 vs. spiked concentration. Heavy isotope labeled internal standard was spiked in plasma at different concentrations prior to immunoaffinity enrichment and LC-MS/MS analysis.

A separate SRM method for murine SDF-1α quantification was also developed. Similar to the SRM method quantifying human SDF-1α forms, four alternating Q1→Q3 transitions were involved with two tracking fragmentation of endogenous murine SDF-1α forms and the other two tracking fragmentation of corresponding heavy isotope labeled human SDF-1α standards. The human heavy standards were used to in lieu of murine heavy standards because of the nearly complete overlap between human and murine SDF-1α sequences with the only difference at position 18 (Val in human, Ile in mouse). The same enrichment antibody was also used in the murine SDF-1α assay. A similar reverse standard curve was also constructed for murine SDF-1α assay, the linear range and LOQ of which were determined as the same as the human SDF-1α assay (FIG. 6). In both FIGS. 5 and 6, the horizontal line represents the endogenous concentration of SDF-1α 3-67, which is well above the limit of quantification and within the linear range of the curve. The level of endogenous SDF-1α 3-67 of murine SDF-1α in pooled plasma was determined as 1.89 nmol/L (% CV=5.2%, N=12), which is within the linear range of the analysis.

Figure 7:
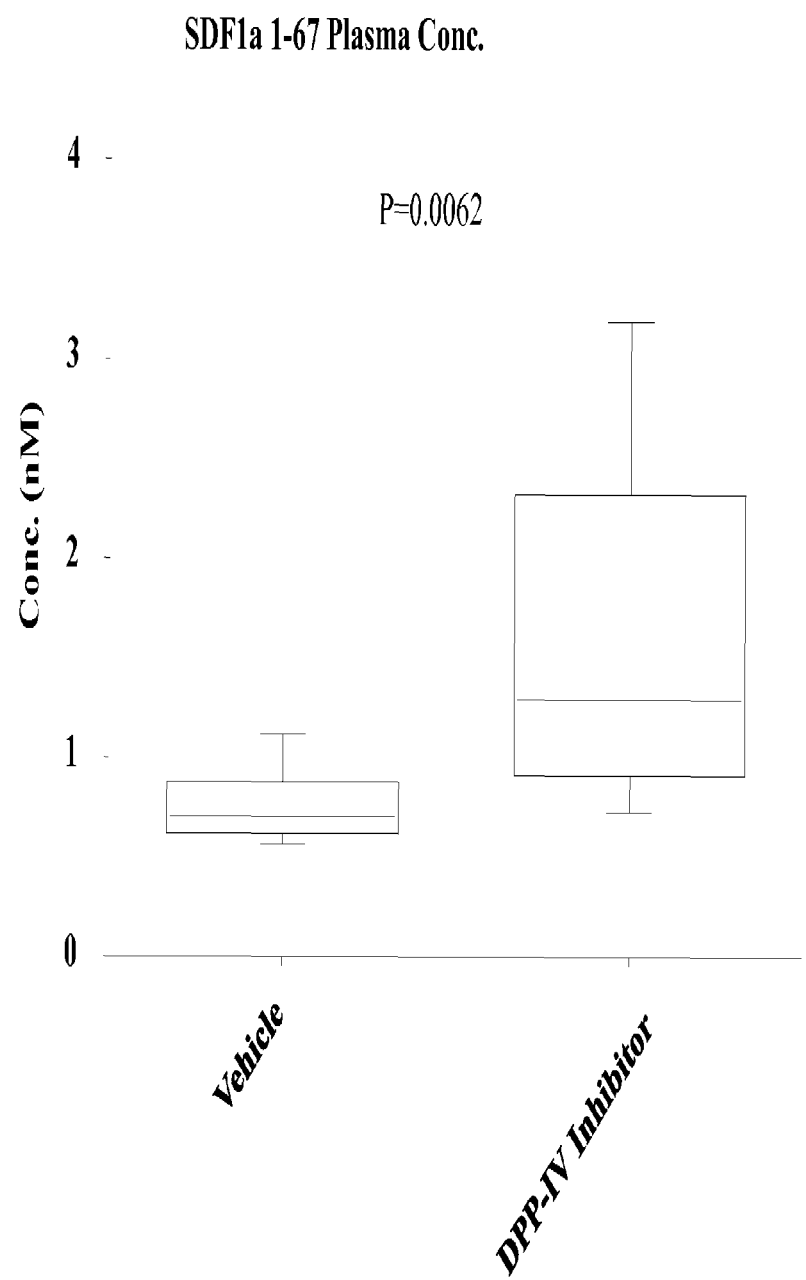
FIG. 7 represents box and whisker plots of levels of intact SDF-1α in mice treated with vehicle or a DPP-IV inhibitor.
Figure 8:
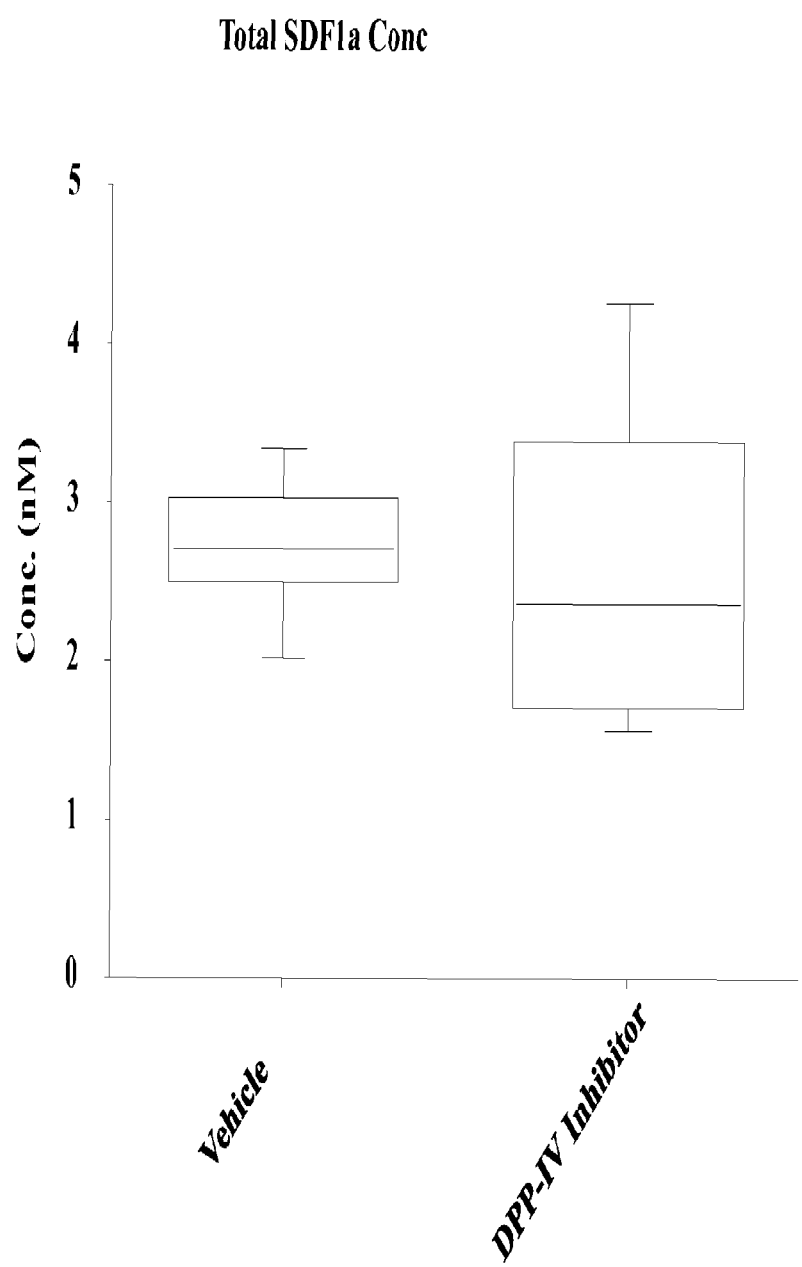
FIG. 8 represents box and whisker plots of levels of total SDF-1α in mice treated with vehicle or a DPP-IV inhibitor.

Suppression of Inactive SDF-1α by DPP-IV Inhibition in an In Vivo Study with Mice Although in vitro studies showed that SDF-1 isoforms (α and β) are good substrates for DPP-IV and ex vivo studies with sera from DPP-IV-deficient mice confirmed the finding, no in vivo studies have been carried out to explore the effect of DPP-IV inhibition on the balance between endogenous SDF-1α active and inactive forms. The main obstacle to such study was the lack of sensitive analytical methods that differentiate the intact SDF-1α from the DPP-IV cleaved inactive form. Since the LC-MS/MS method offered a LOQ much lower than the endogenous level of SDF-1α in pooled murine plasma, suppression of inactive SDF-1α (3-67) by DPP-IV inhibition in an in vivo study using mice was conducted. Plasma samples were collected from lean C57BL/6 mice treated either with a DPP-IV inhibitor or vehicle (N=8 in each group). Intact and NH$_2$-terminal truncated SDF-1α forms were quantified and the results in box and whisker plots are presented in FIGS. 7 and 8. Levels of intact SDF-1α in vehicle group compared with the treatment group, with mean levels being 0.76 nM and 1.54 nM respectively (N=8 in both groups, P=0.0062). Levels of total SDF-1α are the sum of SDF-1α 1-67 and 3-67, in vehicle group and the treatment group. There was a statistically significant difference (P=0.0062) in the level of intact SDF-1α between treatment and vehicle groups with means being 1.54 and 0.76 nM respectively. The total SDF-1α level (the sum of SDF-1α 1-67 and SDF-1α 3-67), however, did not exhibit a statistically significant difference between the treatment and vehicle groups with means being 2.53 and 2.72 nM respectively. This observation highlighted the importance of the development of a specific assay that differentiates the two SDF-1α forms; no effects of DPP-IV inhibition on SDF-1α would have been detected if the assay could not differentiate the two forms and only measure total concentration.

Figure 9:
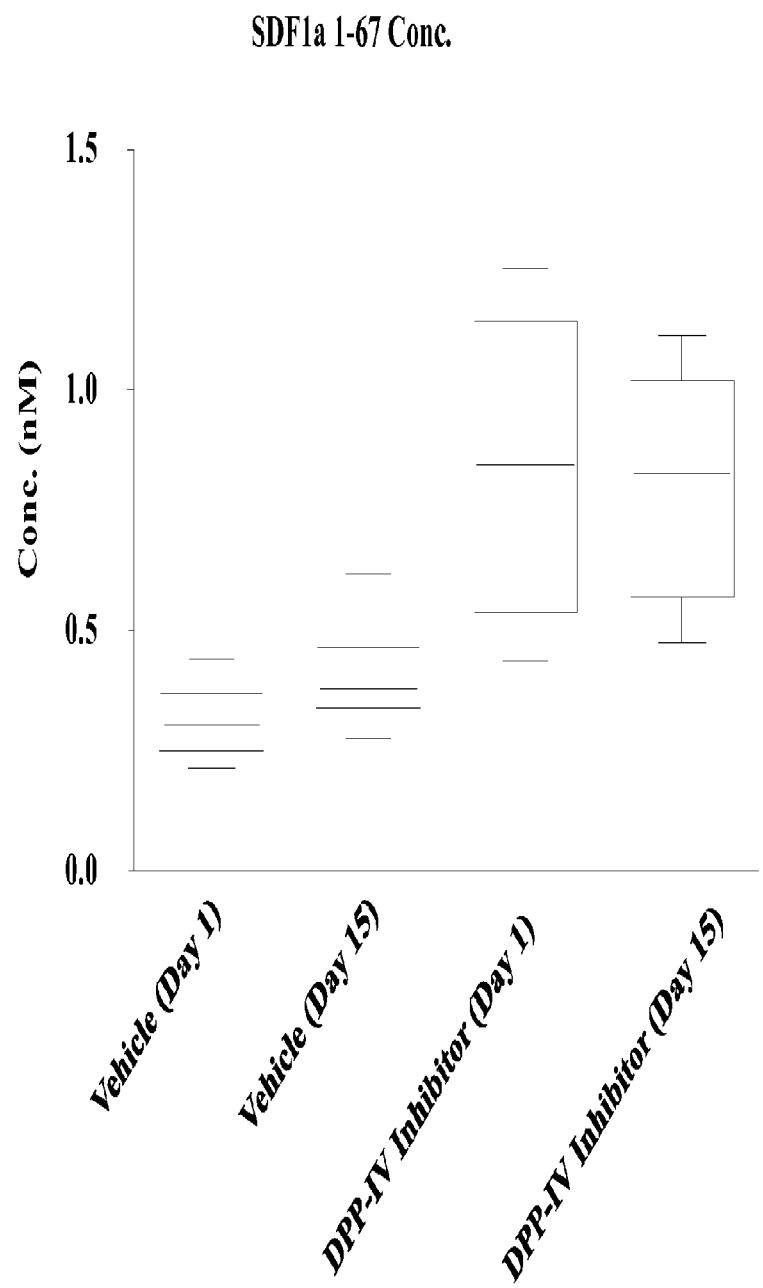
FIG. 9 represents box and whisker plots of levels of intact SDF-1α in rhesus monkeys treated with vehicle or a DPP-IV inhibitor.
Figure 10:
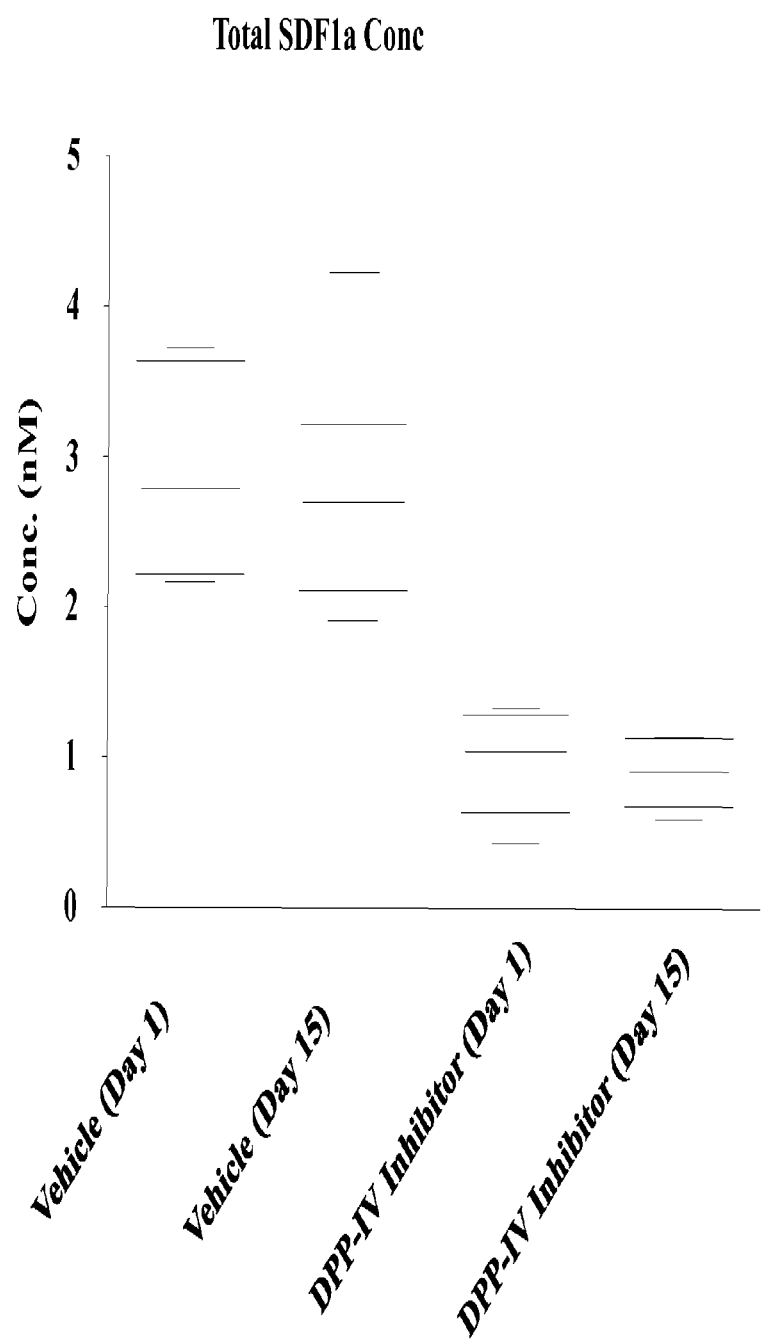
FIG. 10 represents box and whisker plots of levels of total SDF-1α in rhesus monkeys treated with vehicle or a DPP-IV inhibitor.

Suppression of Inactive SDF-1α by DPP-IV Inhibition in an In Vivo Study with Non-Human Primates The effect of DPP-IV suppression on the balance of SDF-1α forms with higher species was also investigated. Plasma samples of rhesus monkeys dosed with vehicle or a DPP-IV inhibitor in acute and chronic fashions were collected for measurements of intact SDF-1α and the truncated form. The results are presented in FIGS. 9-10. Levels of intact SDF-1α in vehicle groups compared with treatment groups (N=6 in all groups), dosed either acutely (day 1) or chronically (day 15). From left to right, mean values for each group are 0.31, 0.41, 0.84, and 0.81 nM. In both dosing regimens, rises in the level of intact SDF-1α in the treatment groups are statistically significant, whereas there is no statistically significant difference in comparisons between dosing regimens within the vehicle or the treatment groups. Levels of total SDF-1α in vehicle groups and treatment groups. From left to right, mean values for each group are 2.89, 2.77, 0.97, and 0.90 nM. The decreases in the level of total SDF-1α in the treatment groups compared with the vehicle group are statistically significant; within the vehicle or the treatment groups, there is no statistically significant difference in comparisons between dosing regimens.

In both acute (day 1) and chronic dosing (day 15), similar to the murine study, there were statistically significant differences in the level of intact SDF-1α between the treatment and vehicle groups. The total SDF-1α level, however, exhibited a statistical significant decrease from the vehicle groups to the treatment groups in both acute dosing and chronic dosing.

The invention claimed is:

1. A method for determining endogenous levels of stromal cell-derived factor 1 (SDF-1) isoforms in vivo comprising the steps of:
   a. preparing a mixture of internal standard of SDF-1 isoforms, wherein the internal standard SDF-1 isoforms includes intact SDF-1 isoforms and NH$_2$-terminal truncated SDF-1 isoforms, a plasma sample containing endogenous SDF-1, wherein the plasma sample is from a subject and wherein the endogenous levels of SDF-1 includes intact SDF-1 isoforms and NH$_2$-terminal truncated SDF-1 isoforms and an immobilized antibody;
   b. incubating the mixture;
   c. separating out the immobilized antibody bound with SDF-1 isoforms;
   d. releasing the SDF-1 isoforms from the immobilized antibody;
   e. introducing the SDF-1 isoforms to a mass spectrometer; and
   f. detecting the amount of endogenous in vivo levels of the SDF-1 isoforms wherein detection of the endogenous levels of SDF-1 includes detection of intact SDF-1 isoforms and $NH_2$-terminal truncated SDF-1 isoforms.

2. The method of claim 1 wherein an intact SDF-1 isoform is SDF-1α.

3. The method of claim 1 wherein an intact SDF-1 isoform is SDF-β.

4. The method of claim 1 wherein the immobilized antibody is a SDF-1α antibody immobilized on a magnetic bead.

5. The method of claim 1 wherein the plasma sample is from a human.

6. The method of claim 1 wherein the plasma sample is from a mouse.

7. The method of claim 1, wherein the linear range spans three orders of magnitude.

8. The method of claim 1, wherein the amount of endogenous levels of the SDF-1 isoforms spans picamolar per liter to nanomolar per liter.

9. The method of claim 1, wherein the method is capable of detecting SDF-1 at concentrations of less than 5 nmol/L in the sample.

10. The method of claim 1, wherein the method is capable of detecting SDF-1 at concentrations of less than 2 nmol/L in the sample.

11. The method of claim 1, wherein the method is capable of detecting SDF-1 at concentrations of less than 1 nmol/L in the sample.

12. A method for determining suppression of inactive stromal cell-derived factor (SDF-1) isoforms by dipeptidyl peptidase-4 (DPP-IV) inhibition in vivo comprising the steps of:
   a. drawing a first plasma sample from a subject;
   b. administering to the subject a DPP-IV inhibitor;
   c. drawing a second sample from the subject;
   d. assaying the first and second sample with the assay as described in claim 1; and
   e. comparing the amount of intact SDF-1 isoforms from the DPP-IV cleaved $NH_2$-terminal truncated SDF-1 isoforms.

13. The method of claim 12, wherein the subject is human.

14. The method of claim 12, wherein the subject is a mouse.

15. The method of claim 12 wherein an intact SDF-1 isoform is SDF-1α.

16. The method of claim 12 wherein an intact SDF-1 isoform is SDF-β.

* * * * *